United States Patent
Castro

(10) Patent No.: US 11,553,945 B2
(45) Date of Patent: Jan. 17, 2023

(54) IMPLANT FOR BONE

(71) Applicant: Blue Sky Technologies, LLC, Louisville, KY (US)

(72) Inventor: Frank Castro, Louisville, KY (US)

(73) Assignee: BLUE SKY TECHNOLOGIES, LLC, Louisville, KY (US)

( * ) Notice: Subject to any disclaimer, the term of this patent is extended or adjusted under 35 U.S.C. 154(b) by 0 days.

(21) Appl. No.: 17/405,119

(22) Filed: Aug. 18, 2021

(65) Prior Publication Data

US 2021/0378712 A1    Dec. 9, 2021

Related U.S. Application Data

(63) Continuation-in-part of application No. PCT/US2019/054383, filed on Oct. 3, 2019.

(60) Provisional application No. 62/809,670, filed on Feb. 24, 2019.

(51) Int. Cl.
*A61B 17/70* (2006.01)
*A61B 17/16* (2006.01)

(52) U.S. Cl.
CPC .......... *A61B 17/70* (2013.01); *A61B 17/1671* (2013.01); *A61B 17/7047* (2013.01); *A61B 17/7074* (2013.01)

(58) Field of Classification Search
CPC .................. A61B 17/7047; A61B 17/7074
USPC ................................................ 606/250–330
See application file for complete search history.

(56) References Cited

U.S. PATENT DOCUMENTS

| | | | |
|---|---|---|---|
| 3,887,186 A | 2/1975 | Matlock, Jr. | |
| 4,244,689 A | 1/1981 | Ashman | |
| 4,913,144 A * | 4/1990 | Del Medico | A61B 17/0642 411/457 |
| 5,395,372 A * | 3/1995 | Holt | A61B 17/7059 606/75 |
| 5,662,655 A * | 9/1997 | Laboureau | A61B 17/0642 606/301 |
| 6,159,211 A | 12/2000 | Boriani et al. | |
| 6,447,525 B2 | 9/2002 | Follmer et al. | |
| 6,743,255 B2 | 5/2004 | Ferree | |
| 6,746,484 B1 | 6/2004 | Liu et al. | |
| 8,070,819 B2 | 12/2011 | Aferzon et al. | |
| 8,100,972 B1 | 1/2012 | Bruffey et al. | |
| 8,199,972 B2 | 6/2012 | Erickson | |
| 9,636,232 B2 | 5/2017 | Neubardt | |
| 9,707,100 B2 | 7/2017 | Afferzon et al. | |
| 9,814,483 B2 | 11/2017 | Vardi | |
| 9,867,733 B2 | 1/2018 | Mohan et al. | |
| 2004/0078079 A1 | 4/2004 | Foley | |
| 2004/0133279 A1 | 7/2004 | Krueger et al. | |
| 2005/0119753 A1 | 6/2005 | McGahan et al. | |
| 2006/0217713 A1* | 9/2006 | Serhan | A61B 17/7022 606/272 |
| 2009/0254125 A1 | 10/2009 | Predick | |
| 2009/0265006 A1 | 10/2009 | Seifert et al. | |

(Continued)

FOREIGN PATENT DOCUMENTS

WO    WO2001085069    11/2001

*Primary Examiner* — Eduardo C Robert
*Assistant Examiner* — Tara Rose E Carter
(74) *Attorney, Agent, or Firm* — Business Patent Law, PLLC

(57) ABSTRACT

The present invention is an implant for bone. The current implant is particularly useful in spinal surgical procedures.

24 Claims, 8 Drawing Sheets

(56) References Cited

U.S. PATENT DOCUMENTS

| | | | |
|---|---|---|---|
| 2010/0280622 A1* | 11/2010 | McKinley | A61F 2/4455 623/17.16 |
| 2011/0144694 A1* | 6/2011 | Laeng | A61B 17/7037 606/86 A |
| 2011/0264229 A1 | 10/2011 | Donner | |
| 2012/0010659 A1 | 1/2012 | Angert et al. | |
| 2012/0232599 A1 | 9/2012 | Schoenly et al. | |
| 2013/0150906 A1 | 6/2013 | Kerboul et al. | |
| 2014/0172103 A1* | 6/2014 | O'Neil | A61F 2/4611 623/17.16 |
| 2016/0184099 A1* | 6/2016 | Gotfried | A61F 2/30734 623/18.11 |
| 2016/0310294 A1 | 10/2016 | McConnell et al. | |

\* cited by examiner

IMPLANT FOR BONE

PRIORITY

Applicant claims priority to PCT/US2019/054383—Implant for Bone—, filed Oct. 3, 2019 that claims the benefit of U.S. Provisional Application No. 62/809,670—Implant for Bone—filed on Feb. 24, 2019.

BACKGROUND OF THE INVENTION

A. Field of the Invention

Among other things, the present invention is an implant for bone. The current implant is particularly suited for implantation into mammalian spinal tissues. The present implant is provided with a cutting blade or surgical cutter. Select embodiments of the current invention include surface treatments in anticipation of improving attachment of bone to the implant.

B. Description of the Previous Art

Any discussion of references cited in this Description of the Previous Art merely summarizes the disclosures of the cited references and Applicant makes no admission that any cited reference or portion thereof is relevant prior art. Applicant reserves the right to challenge the accuracy, relevancy and veracity of the cited references.

References that may indicate a state-of-the-art for the current invention include: 1) U.S. Pat. No. 9,814,483-Vardi discloses a method and catheter for creating an interatrial aperture; 2) U.S. Pat. No. 3,887,186-Matlock, Jr. disclose a broadhead; 3) U.S. Pat. No. 8,199,972-Bruffey, et al. discloses a spinal cage having deployable member; 4) U.S. Pat. No. 4,244,689-Ashman discloses an endosseous plastic implant; 5) US Published Patent Application 20120232599-Schoenly, et al. discloses awl screw fixation members and related systems; 6) U.S. Pat. No. 9,636,232-Neubart discloses harvesting bone graft material for use in spinal and other bone fusion surgeries; 7) US Published Patent Application 20120010659-Angert, et al. discloses a facet fusion implant; 8) U.S. Pat. No. 6,447,525-Follmer, et al. discloses an apparatus and methods for removing material from a body lumen; 9) U.S. Pat. No. 8,070,819-Aferzon, et al. discloses an apparatus and method for anterior intervertebral spinal fixation and fusion; 10) U.S. Pat. No. 9,707,100-Duffield, et al. disclose an interbody fusion device and system for implantation; 11) U.S. Pat. No. 9,867,733-Mohan, et al. discloses a tissue adjustment implant; 12) US Published Patent Application 20040078079-Foley discloses systems and techniques for restoring and maintaining intervertebral anatomy; 13) US Published Patent Application 20090265006-Seifert, et al. discloses a lateral spinous process spacer; 14) US Published Patent Application 20160184099-Gotfried; 15) US Published Patent Application 20110264229-Donner discloses a sacroiliac joint fixation system; 16) US Published Patent Application 20130150906-Kerboul, et al. discloses a system and method for a lockable polyaxial driver tool; 17) US Published Patent Application 20090254125-Predick discloses a top loading polyaxial spine screw assembly with one step lockup; 18) WO2001085069-Lemaire, et al. discloses an anterior lumbar interbody implant; 19) U.S. Pat. No. 6,159,211-Boriani et al. discloses a stackable cage system for corpectomy/vertebrectomy; 20) U.S. Pat. No. 6,743,255-Ferree discloses a spinal fusion cage with lordosis correction; 21) U.S. Pat. No. 6,746,484-Liu, et discloses a spinal implant; 22) US Published Patent Application 20040133279-Kruger, et al. discloses surgical implants for use as spinal spacers; 23) US Published Patent Application 2005/0119753-McGahan, et al. discloses an anterior impacted bone graft and driver instruments; and 24) 20160310294-McConnell et al. discloses a spinal fusion implant for oblique insertion.

SUMMARY OF THE INVENTION

The present invention provides a biocompatible implant for bone that can be interlocked with a device distinct from the implant. The current implant is also provided with a blade for cutting tissue. Preferred embodiments of the current fastener can also be utilized for transporting biocompatible devices/substances, such as adhesives, electrode leads, cannulas, fiber optics, implants, pharmaceuticals, etc. Preferred embodiments of the implant's blade are provided with an aperture. The aperture can assist tissue growth, such as bone, into and through the implant as well onto the inward surfaces of the implant. Select embodiments of the implant are provided with surface treatments in anticipation of improving attachment of bone to the implant.

With regard to spinal surgical procedures, prior art traditional fixation screws fixation stability is dependent on the healthy composition of the cancellous bone. Those skilled in the art recognize the healthy cortical bone is from about 20 to about 100 times stronger than healthy cancellous bone. Those skilled in the art also know that increasing the screw length for osteoporotic bone rarely provides satisfactory resistance against the fixation screw from pulling-out or backing-out of bone. The blade of the current implant is shorter and wider than traditional fixation screws. Because of its novel structure and surgical insertion technique, the present implant has greater resistance against pulling-out or backing-out of osteoporotic bone. Further still, the blade's shorter length reduces the possibility of injury to nearby structures such as arteries, veins and nervous tissues. It is believed that the current invention's resistance to pull-out or back-out improves implant-construct stability, higher bone fusion rates and better postoperative clinical outcomes than prior art fixation screws.

For surgical procedures involving bone, the current implant can be inserted through a small linear aperture into the bone tissue. In one of the preferred uses of the current implant, subsequent to blade's surgical insertion into bone, the blade can be rotated up to 90 degrees relative to the plane of the surgical incision. Among other things, rotation of the blade increases resistance against pull-out or back-out of the blade from bone when compared to prior art fixation screws. It is also believed that the width of the implant's blade can contact a greater surface area of healthier cortical bone distinct from the surgically created cavity, thereby improving the possibility of successful postoperative bone fusion relative to prior art fixation screws.

Within the scope of the current invention, blades can be of symmetrical or asymmetrical configuration.

Symmetrical blades are typically preferred when the inner cortex is straight—a straight inner cortex as viewed from a lateral X-ray perspective looking at the spine. Asymmetrical blades are generally preferred when the inner cortex is sloped as seen on a lateral X-ray or sagittal CT scan). Regardless of whether symmetrical or asymmetrical, implants within the scope of the current invention require insertion and subsequent rotation of the blade of up to 90 degrees relative to the plane of the surgical incision.

In use, any surgical connecting rods will generally be parallel to the blades. In a first example for a laminectomy and fusion procedure, connecting rods and the present implant's blades will be generally vertical. In a second example for a laminoplasty procedure, the connecting rods and current implant's blades will be horizontal extending from the right side of the spinal elements to the left side spinal elements. The surgical incision will be up to 90 degrees offset from the final orientation of the implant's blade.

Various asymmetrical blade configurations are typically preferred when the surgical insertion corridor is not cylindrical. By way of illustration, when the current device is implanted into the posterior cervical facets, the blade is initially inserted through the posterior cortex perpendicular to the axis of the spinal cord. After insertion, the blade is rotated up to 90 degrees to be parallel to the axis of the spinal cord. It is believed that the asymmetrical blade allows for a greater surface area contact of the posterior cortex.

An aspect of the present invention is to provide an implant with a cutting blade.

Still another aspect of the present invention is to provide an implant with a blade that can be rotated up to 90 degrees relative to the surgical incision.

It is still another aspect of the present invention to provide an implant that improves resistance to pull-out or back-out and improves implant-construct stability, higher bone fusion rates and better postoperative clinical outcomes than prior art fixation screws.

Yet still another aspect of the present invention is to provide an implant with greater resistance against pulling-out or backing-out of osteoporotic bone that current fixation screws.

Still another aspect of the present invention is to provide an implant adapted for connection with a device distinct from the implant.

Yet another aspect of the present invention is to provide an implant with a conduit for transporting biocompatible devices/substances or chemotherapeutic agents.

It is still another aspect of the present invention to provide an implant with a blade having an aperture therein.

Yet still another aspect of the present invention is to provide an implant adaptable for use in the cervical region of the spine.

Still another aspect of the present invention is to provide an implant with a surgical cutter including a common bend.

It is still another aspect of the present invention to provide an implant adapted to cut in a forward, a clockwise or a counterclockwise direction.

Yet another aspect of the present invention is to provide an implant first and second segments where each segment has different slopes.

A preferred embodiment of the current invention can be described as an implant (220) for bone adapted for interconnection with a device distinct from the implant (220); the implant (220) comprising: a) a shaft (240) comprising a first end (242) and a second end (244) opposite the first end (242); the shaft (240) including a first longitudinal axis (X-X) therein and extending away from the first end (242) and the second end (244); and b) a surgical cutter (300) comprising: i) a first segment (310) extending away from the first longitudinal axis (X-X) in a first direction and a second segment (320) extending away from the longitudinal axis (X-X) in a second direction, wherein the first segment (310) and the second segment (320) include a second longitudinal axis (Y-Y); ii) a first surface (352) and a second surface (354) opposed from the first surface (352); the first and second surfaces (352, 354) separated by a width (330), wherein the width (330) is greater proximate the first longitudinal axis (X-X) and lesser remote from the longitudinal axis (X-X) such that the first segment (310) and the second segment (320) comprise different slopes (332, 334); iii) a first side (356) connected, at an angle oblique to the longitudinal axis (X-X), to a first end (242) of the shaft (240); iv) a second side (362) parallel to the first side (356) for a length of the first segment (310); v) a third side (368) extending between the first and second surfaces (352, 354) and first and second sides (356, 362); vi) a fourth side (370) extending between the first and second surfaces (352, 354) and the first and second sides (356, 362), wherein the width (330) is enclosed by the first and second surfaces (352, 354) and the first, second, third and fourth sides (356, 362, 368, 370); and vii) at least one cutting edge (380) incorporated onto the second side (362) and the fourth side (370); the cutting edge (380) connected to the first surface (352), the second surface (354), the second side (362) and fourth side (370).

Another preferred embodiment of the current invention can be described as an implant (220) for bone adapted for interconnection with a device distinct from the implant (220); the implant (220) comprising: a) a shaft (240) comprising a first end (242) and a second end (244) opposite the first end (242); the shaft (240) including a first longitudinal axis (X-X); and b) a surgical cutter (300) comprising: i) a first surface (352) and a second surface (354) opposed from the first surface (352); the first surface (352) and the second surface (354) separated by a shared width (330) and the shared width (330) comprising a least one common bend (390); ii) a first side (356) connected, at an angle oblique to the longitudinal axis (X-X), to a first end (242) of the shaft (240); iii) a second side (362) parallel to the first side (356); iv) a third side (368) extending between the first and second sides (356, 362); v) a fourth side (370) extending between the first and second sides (356, 362); and vi) at least one cutting edge (380) incorporated onto the second side (362) and the fourth side (370).

Yet another preferred embodiment of the current invention can be described as an implant (210) for bone adapted for interconnection with a device distinct from the implant (210); the implant (210) comprising: a) a surgical cutting wedge (250) comprising: i) a first planar surface (252) and a second planar surface (254); ii) an interconnected combination of a first side (256), a second side (260) and a third side (268); the interconnected combination of the first, second and third sides (256, 260, 268) extending between and connected to the first and second planar surfaces (252, 254), wherein: the first side (256) comprises a first end (258) of greater height than an opposed second end (260) of first side (256); and the second side (262) comprises a first end (264) of greater height than an opposed second end (266) of second side (262); iii) a cutting edge (280) connected to the first and second planar surfaces (252, 254) and the second ends (260, 266) of the first and second sides (256, 262) such that the cutting edge (280) is adapted to cut in perpendicular, clockwise and counterclockwise directions relative to a shaft (240); and iv) a channel (248), positioned proximate to the cutting edge (280), extending through the surgical cutting wedge (250); and b) a first end (242) of a shaft (240) connected to the first side (256) of the surgical cutting wedge (250).

It is the novel and unique interaction of these simple elements which creates the apparatus and methods, within the ambit of the present invention. Descriptions of preferred embodiments of the invention follow. However, it is to be

DESCRIPTION OF THE PREFERRED EMBODIMENTS

Figure 1:
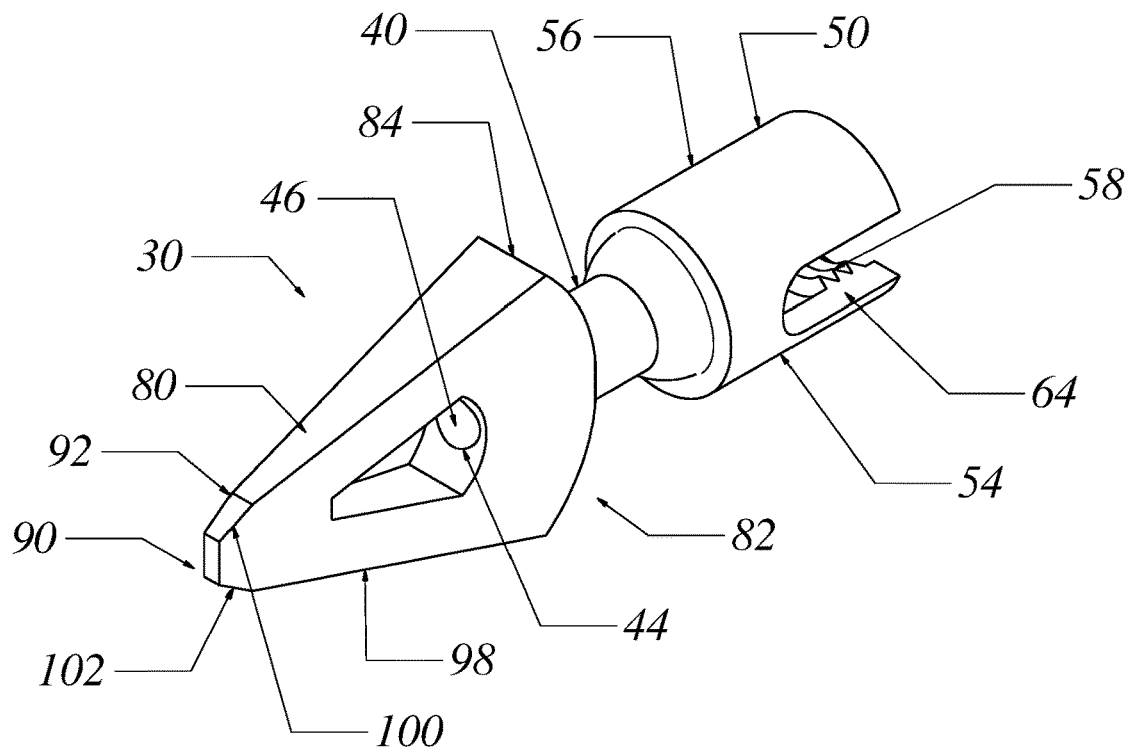
FIG. 1 is a perspective of a first preferred embodiment of the implant.

Although the disclosure hereof is detailed to enable those skilled in the art to practice the invention, the embodiments published herein merely exemplify the present invention.

In the most general sense, the present invention is an implant for bone where the implant is adapted for connection with a device distinct from the implant. Among other things, the current invention can be adapted for use with vertebra or other bone tissues. The present implant is particularly adapted for use in the cervical region of the spine. The current invention can be provided with a conduit for transporting biocompatible devices/substances or chemotherapeutic agents, such as adhesives, electrode leads, cannulas, fiber optics, implants, pharmaceuticals, etc. Dispersion of adhesives from the windows or openings of the implant before closing the surgical wound, reduces the risk of the fastener backing out of the wound prior to the fastener fully interlocking with tissue overgrowth. Polymethymethacrylate is an adhesive particularly well suited for use with the current fastener.

Preferred embodiments of the present invention are manufactured of titanium alloys, stainless steel, non-resorbable polymers or any other composition acceptable in the art. Within the scope of the present invention, it has advantageously been discovered that cylindrical shafts (40) can have lengths from about 2 to about 10 millimeters; polyaxial heads (50) can have lengths of from about 5 millimeters to about 25 millimeters; sockets (54) of polyaxial heads (50) can have depths from about 3 millimeters to about 23 millimeters, diameters from about 4 millimeters to about 20 millimeters, lateral openings widths (62, 64) from about 3 millimeters to about 10 millimeters; and blades (80, 120) can have lengths of from about 3 millimeters to about 12 millimeters, widths of from about 4 millimeters to about 10 millimeters and heights of from about 0.2 millimeters to about 4 millimeters.

Figure 2:
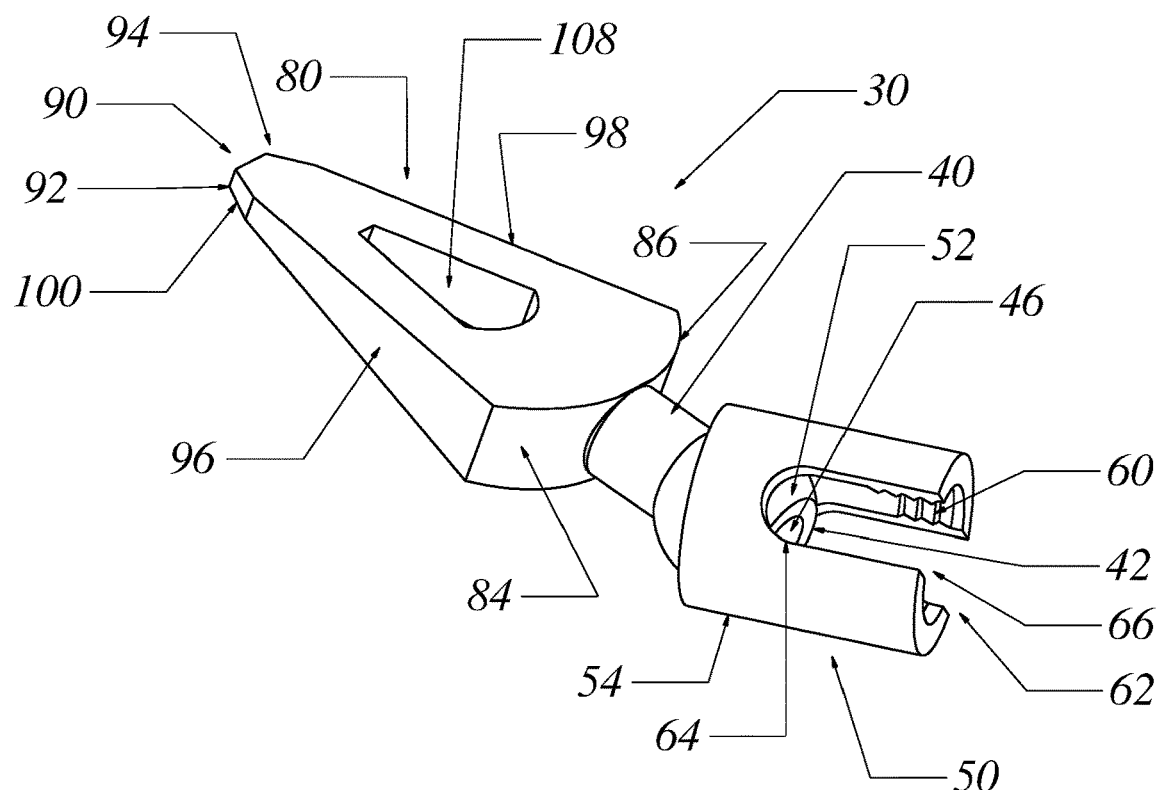
FIG. 2 is a perspective of a first preferred embodiment of the implant.

FIGS. 1 and 2 are perspectives of a first preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 1 and 2, includes cylindrical shaft (40), polyaxial head (50) and blade (80). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (40) include but are not limited to: rods, bars, cross-links, screws and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Arcuate side (82) of blade (80) is connected with second side (44) of cylindrical shaft (40). Arcuate side (82) of blade (80) is of a dimension wider than the diameter of cylindrical shaft (40). Arcuate side (82) includes first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial, osteogenic or chemotherapeutic substances into the surgically created cavity.

Figure 3:
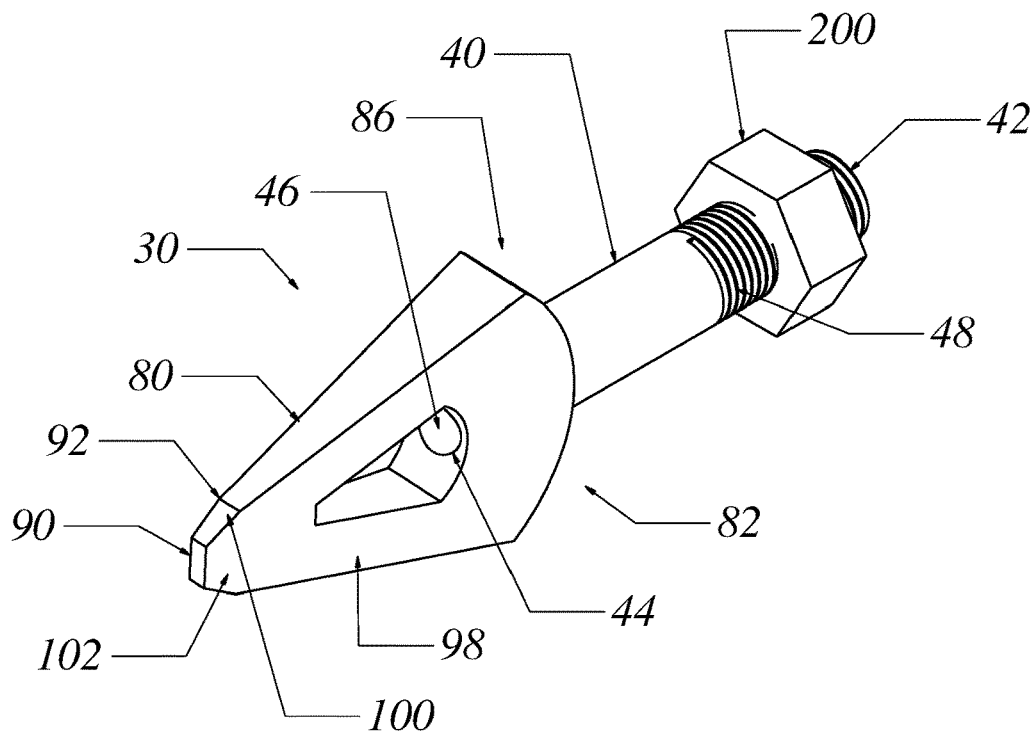
FIG. 3 is a perspective of a second preferred embodiment of the implant.
Figure 4:
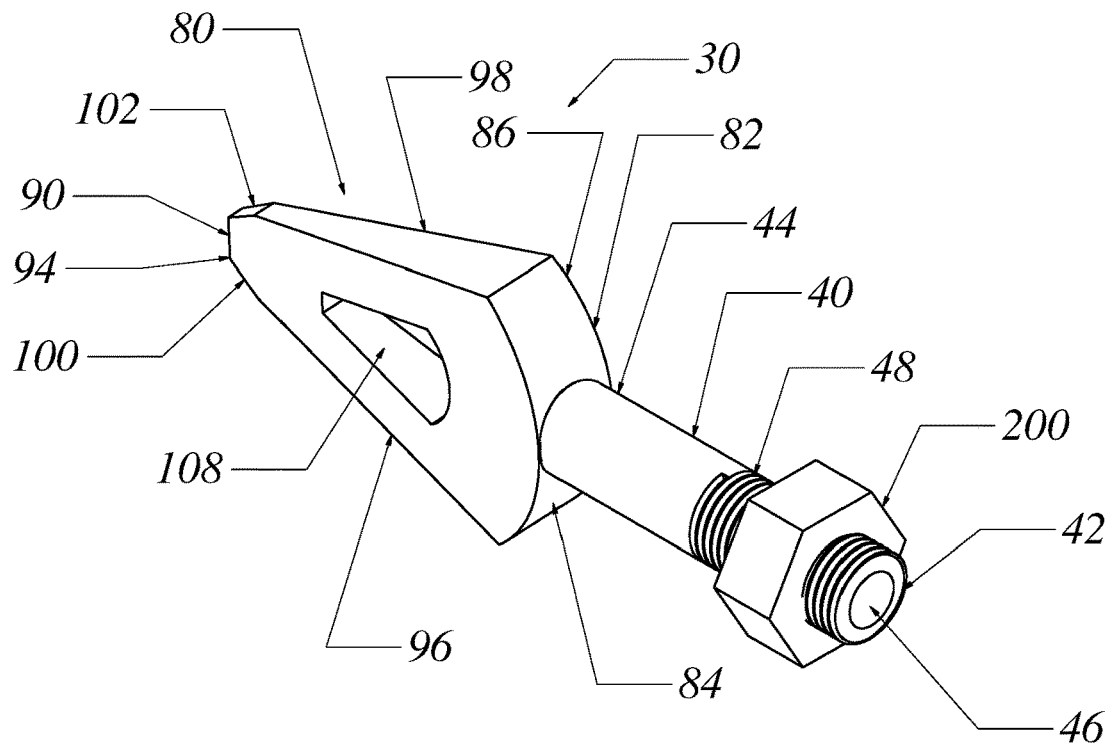
FIG. 4 is a perspective of a second preferred embodiment of the implant.

FIGS. 3 and 4 are perspectives of a second preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 3 and 4, includes cylindrical shaft (40) and blade (80). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Arcuate side (82) of blade (80) is connected with second side (44) of cylindrical shaft (40). Arcuate side (82) of blade (80) is of a dimension wider than the diameter of cylindrical shaft (40). Arcuate side (82) is also provided with first wing (84) and second wing (86) where each wing (84, 86) extends away from the longitudinal axis of cylindrical shaft (40). As shown in FIGS. 1 and 2, each wing (84, 86) is arched away from first end (42) of cylindrical shaft (40).

Straight side (90) of blade (80) is of lesser length than arcuate side (82) and positioned opposite from arcuate side (82). Straight side (90) includes first end (92) and second end (94). First converging edge (96) connected to first wing (84) and second converging edge (98) connected second wing (86) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 5:
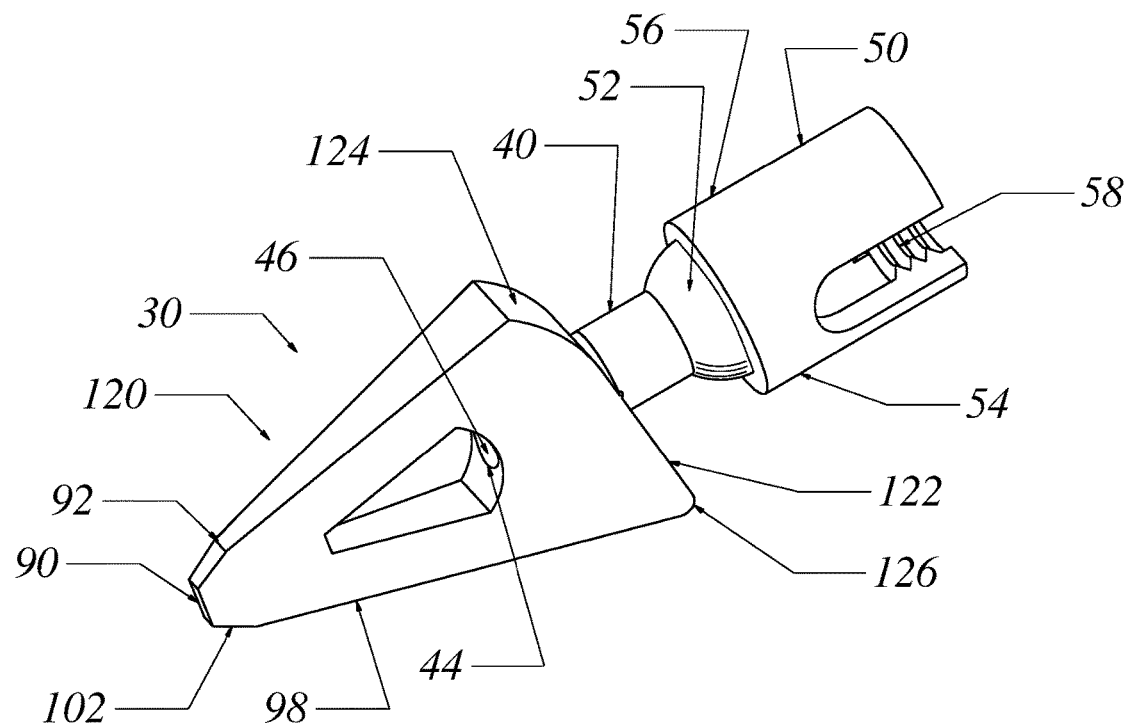
FIG. 5 is a perspective of a third preferred embodiment of the implant.
Figure 6:
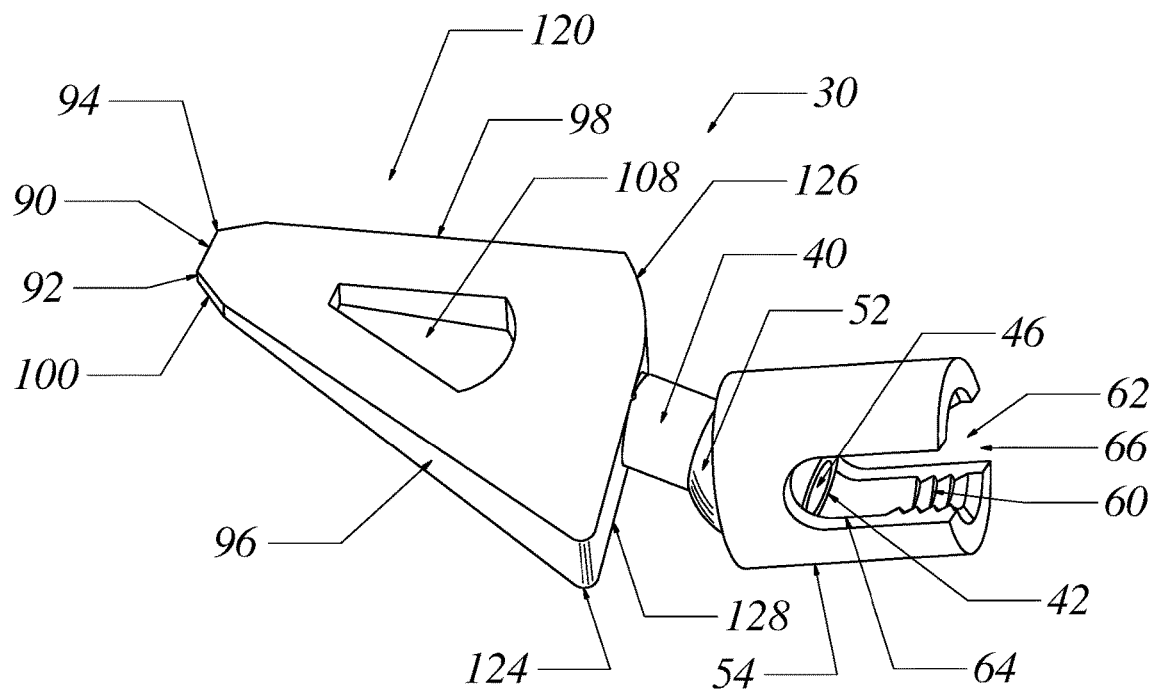
FIG. 6 is a perspective of a third preferred embodiment of the implant.

FIGS. 5 and 6 are perspectives of a third preferred embodiment of implant (30). Within the scope of the current invention, implant (30) can be interconnected with a device distinct from the implant. It has been discovered that implant (30) is useful for spinal surgeries, and, in particular, surgeries for the cervical region of the spine.

Among other things, the preferred embodiment of implant (30), enabled in FIGS. 5 and 6, includes cylindrical shaft (40), polyaxial head (50) and blade (120). Cylindrical shaft (40) includes first end (42), second end (44) and inner cavity (46) extending through first end (42) and second end (44).

Polyaxial head (50) of implant (30) is adapted for connection with a device (not shown) distinct from implant (30). Examples of devices connectable to polyaxial head (50) include but are not limited to: rods, cross-links, bars, screws, and locking nuts. Polyaxial head (50) is provided with spheroid (52) connected to first end (42) of cylindrical shaft (40) and socket (54) connected to spheroid (52). Prior to surgical fixation, the combination of spheroid (52) and socket (54) allows polyaxial head (50) to be moved in a multitude of axes relative to the longitudinal axis or inner cavity (46) of cylindrical shaft (40). Socket (54) is provided with an outward housing (56) and inward receptacle (58) including one or more threads (60). Selected preferred embodiments of housing (56) can be provided with openings (62, 64, 66) adapted to receive one or more devices distinct from implant (30).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 5 and 6, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Figure 7:
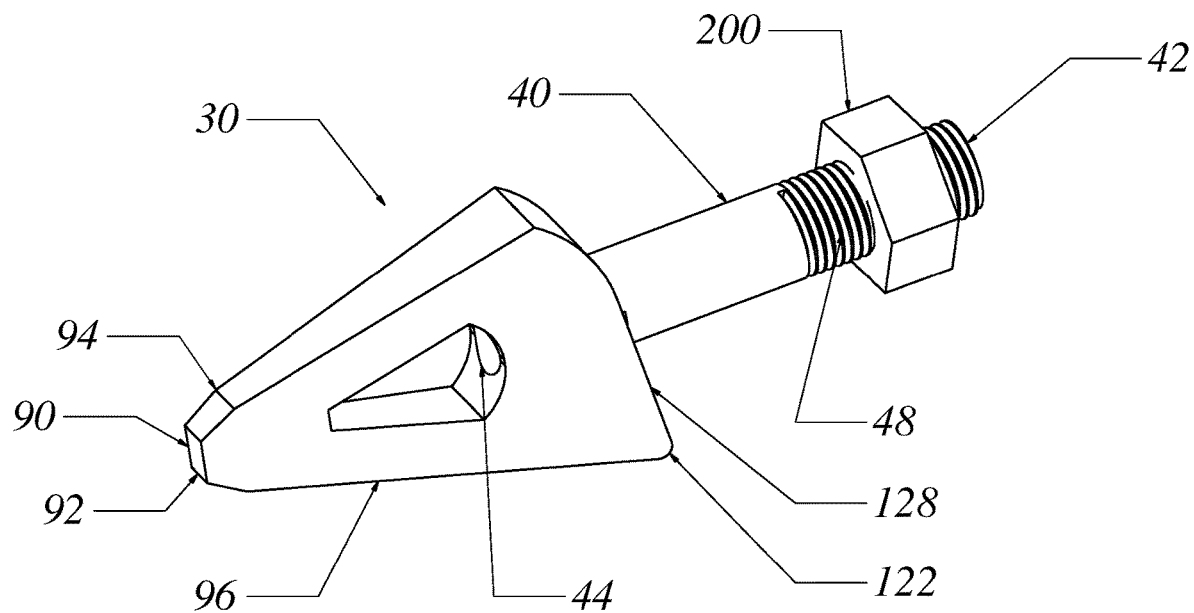
FIG. 7 is a perspective of a fourth preferred embodiment of the implant.
Figure 8:
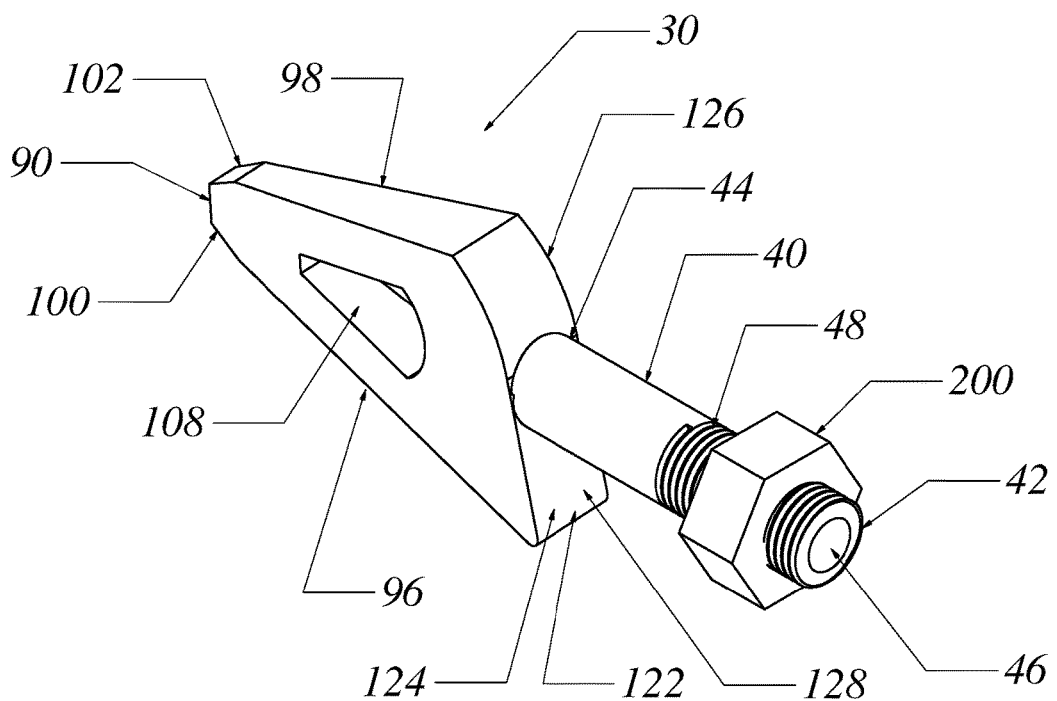
FIG. 8 is a perspective of a fourth preferred embodiment of the implant.
Figure 9:
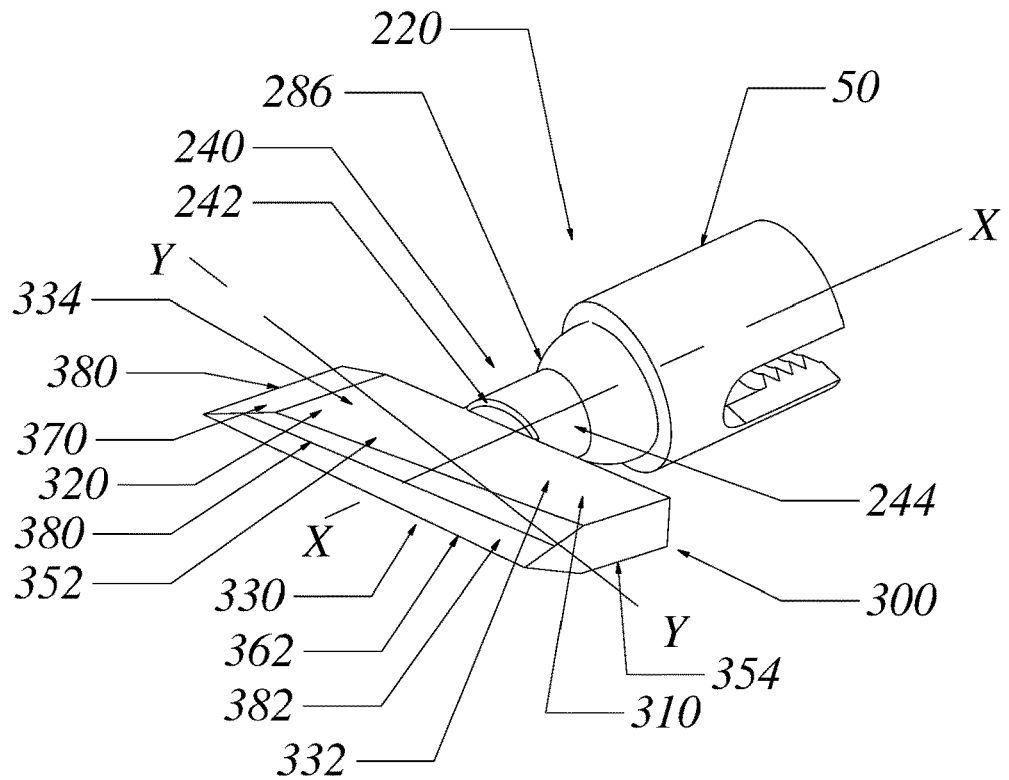
FIG. 9 is a perspective of a fifth preferred embodiment of the implant.
Figure 10:
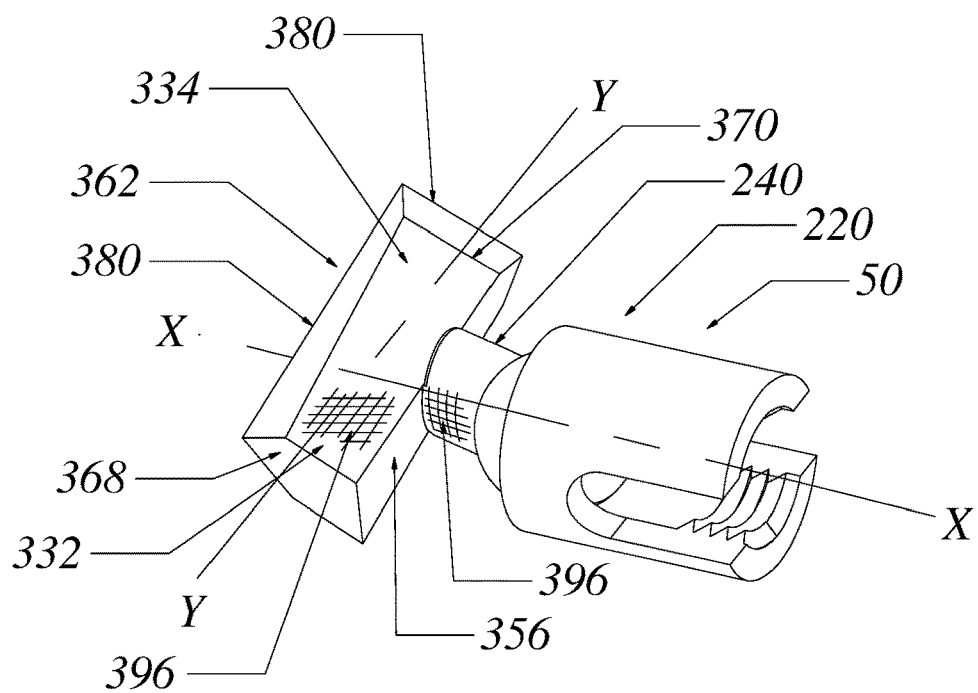
FIG. 10 is a perspective of a fifth preferred embodiment of the implant.
Figure 11:
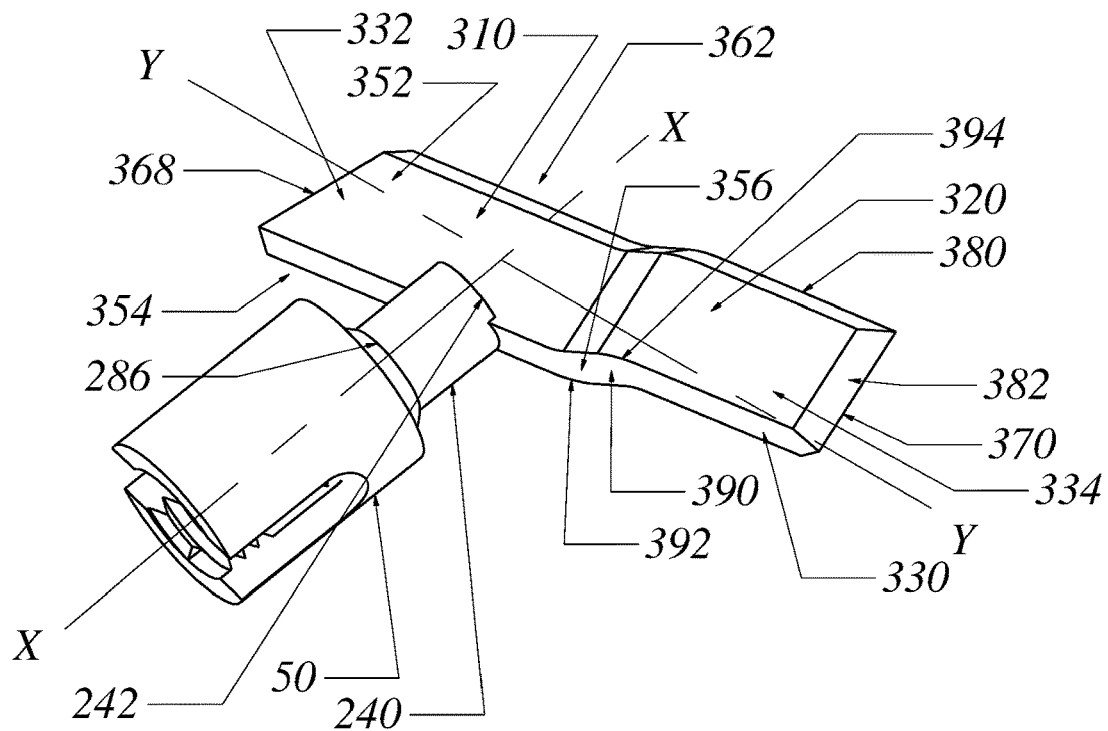
FIG. 11 is a perspective of a fifth preferred embodiment of the implant.
Figure 12:
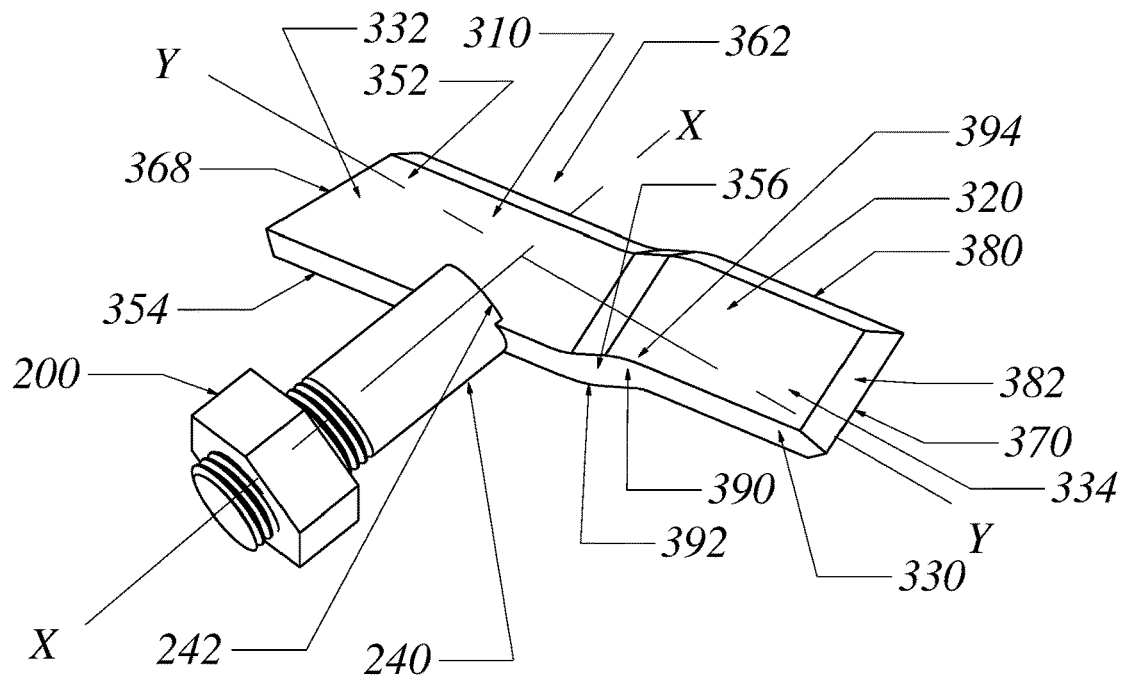
FIG. 12 is a perspective of a sixth fifth preferred embodiment of the implant.

FIGS. 7 and 8 are perspectives of a fourth preferred embodiment of implant (30). Within the scope of the current invention, implant (30) can be interconnected with a device distinct from the implant, such as a nut (200) or other device (not shown) for coupling with implant (30). It has been discovered that implant (30) is useful for spinal surgeries, and, in particular, surgeries for the cervical region of the spine.

Among other things, the preferred embodiment of implant (30), enabled in FIGS. 7 and 8, includes cylindrical shaft (40) and blade (120). Cylindrical shaft (40) includes first end (42), second end (44) and inner cavity (46) extending through first end (42) and second end (44). First end (42) of cylindrical shaft (40) is provided with thread (48) that can be utilized to connect implant (30) to a device distinct from implant (30). Thread (48) runs about at least a portion of the outward side of cylindrical shaft (40) and advances from first end (42) toward the second end (44) of cylindrical shaft (40).

Slanted side (122) of blade (120) is connected with second side (44) of cylindrical shaft (40). Slanted side (122) of blade (120) is of a dimension wider than the diameter of cylindrical shaft (40). Slanted side (122) includes first wing (124) and second wing (126) where each wing (124, 126) extends away from the longitudinal axis of cylindrical shaft (40). As shown in FIGS. 7 and 8, a first one of the wings (124, 126) is arcuate and arched away from the first end cylindrical shaft (40). A second one of the wings (124, 126) is provided with a pitched plane (128) facing first end (42) of cylindrical shaft (40). The combination of an arcuate wing and a wing including a pitched plane creates an asymmetric blade (120). Pitched plane (128) intersects the longitudinal axis of implant (30) at an angle of between five and eighty five degrees as measured from the distal point of pitched plane (128) to the intersection of pitched plane and implant's (30) longitudinal axis.

Straight side (90) of blade (120) is of lesser length than slanted side (122) and positioned opposite from slanted side (122). Straight side (90) includes first end (92) and second end (94). First converging edge (96) connected to first wing (124) and second converging edge (98) connected second wing (126) converge toward each other as the converging edges (96, 98) approach straight side (90). Select preferred embodiments of the current invention can be provided with first transitional edge (100) connected to first end (92) of straight side (90) and first converging edge (96) and second transitional edge (102) second end (94) of straight side (90) and converging edge (98). Within the scope of the current invention, select preferred embodiments of implant (30) are not provided with transitional edges (100, 102) and converging edges (96, 98) are connected directly to first end (92, 94) of straight side (90). Regarding the current implant (30), straight side (90), converging edges (96, 98) and transitional edges (100, 102) are adapted to surgically cut bone and other tissues.

Implant (30) is provided with aperture (108) proximate the center of blade (80). Post implantation, the combination of aperture (108) and inner cavity (46) of cylindrical shaft (40), among other things, allows the surgeon to remove unwanted debris from the surgical wound or introduce adhesive, antimicrobial or osteogenic substances into the surgically created cavity.

Within the scope of the current present invention, select preferred embodiments can be provided with a surgical wedge cutter (250) and a permanent shaft (240) or a releasable shaft (240).

FIGS. 9-12 portray a fifth and sixth embodiments of the current invention. Implant (220) for bone adapted for interconnection with a device distinct from the implant (220) Examples of devices connectable to implant (220) include but are not limited to: rods, bars, cross-links, screws and locking nuts. Select preferred embodiments of implant (220) can include first longitudinal axis (X-X) and second longitudinal axis (Y-Y) where first longitudinal axis (X-X) and second longitudinal axis (Y-Y) intersect at an oblique angle.

Implant (220) includes shaft (240) and surgical cutter (300). In accordance with the present invention, surgical cutter (300) can cut in a forward, a clockwise or a counter-clockwise direction. By way of illustration, forward motion of cutter (300) can penetrate and slice tissue(s) while rotation of shaft (240) causes cutter (300) to cut tissue(s) in either a clockwise or counterclockwise directions.

Shaft (240) has a first end (242) and a second end (244) opposite the first end (242). Select preferred embodiments of implant (210) can include a second end (286) of shaft (240) that comprises a thread (292). Other preferred embodiments of implant (210) can include a polyaxial head (50) connected to second end (244) of shaft (240).

Surgical cutter (300) is connected to the first end (242) of the shaft (240). First longitudinal axis (X-X) can extend away from first end (242) and second end (244) of shaft (240).

Surgical cutter (300) is provided with first segment (310) extending away from the first longitudinal axis (X-X) in a first direction and a second segment (320) extending away from the longitudinal axis (X-X) in a second direction, where the first segment (310) and the second segment (320) include a second longitudinal axis (Y-Y). Surgical cutter (300) includes first surface (352) and a second surface (354) opposed from the first surface (352) separated by width (330).

When engineering parameters require, width (330) of cutter (300) is greater proximate first longitudinal axis (X-X) and lesser remote from longitudinal axis (X-X). First segment (310) of surgical cutter (300) is located on a first side of first longitudinal axis (X-X) and second segment (320) of surgical cutter (300) is located on a second side of first longitudinal axis (X-X). This configuration of first segment (310) and second segment (320) results in different slopes (332, 334) for first and second segments (310, 320). It is believed that such a configuration improves resistance against pullout or back out of implant (220).

First surface (352), second surface (354), third side (368) and fourth side (370) enclose width (330). Second side (362) is parallel to the first side (356) for a length of the first segment (310). Third side (368) extends between the first and second surfaces (352, 354) and first and second sides (356, 362). Fourth side (370) extends between the first and second surfaces (352, 354) and the first and second sides (356, 362). First side (356) is connected, at an angle oblique to longitudinal axis (X-X), to first end (242) of shaft (240). At least one cutting edge (380) is incorporated onto second side (362) and fourth side (370). In select preferred embodiments, cutting edge (380) is connected to first surface (352), second surface (354), second side (362) and fourth side (370). Cutting edge (380) can be provided with bevel (382)

Second segment (320) of surgical cutter (300) can include bend or common bend (390). Depending on medical engineering parameters, second segment (320) can have a greater surface area than first segment (310). In other words, segment (310, 320) with the common bend has a greater surface area that the segment without the bend (390). In select preferred embodiments, bend or common bend (390) is provided with first curve (392) away from second longitudinal axis (Y-Y) and second curve (394) toward second longitudinal axis (Y-Y).

Head (50) is connected to second end (244) of shaft (240). Select preferred embodiments of implant (220) utilize a polyaxial head. For other embodiments, second end (286) of shaft (240) can be provided with thread (292). Thread (292) is adapted to interact with a device distinct from implant (220) such as a nut.

It is believed that the combination of different slopes (332, 334), bend (390) and surface treatments (396) of implant (220) improve resistance against pullout or back out of implant (220) when compared to currently available surgical screws.

Figure 13:
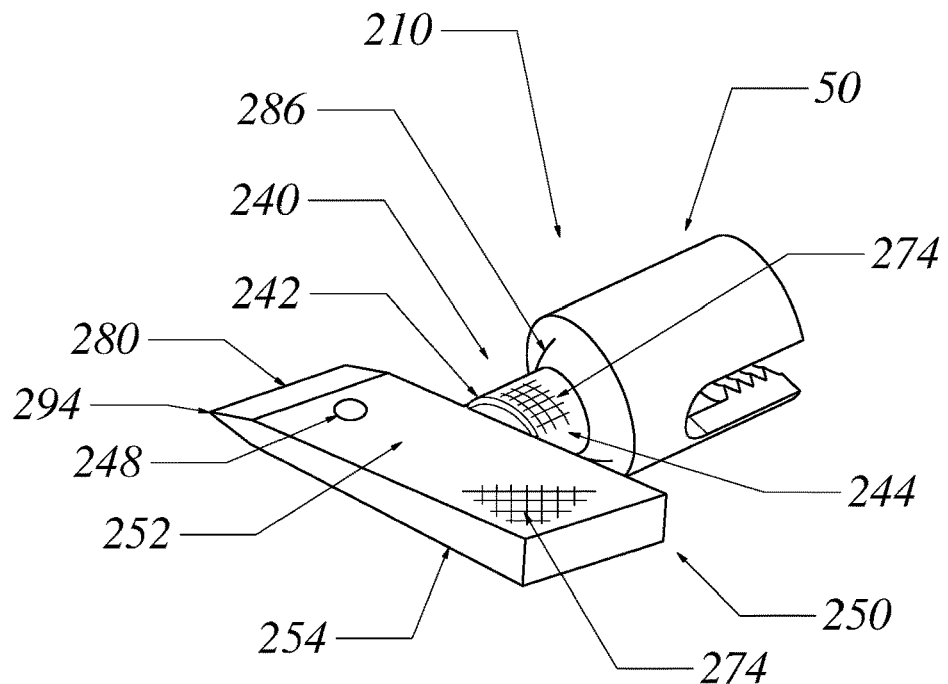
FIG. 13 is a perspective of a seventh preferred embodiment of the implant.
Figure 14:
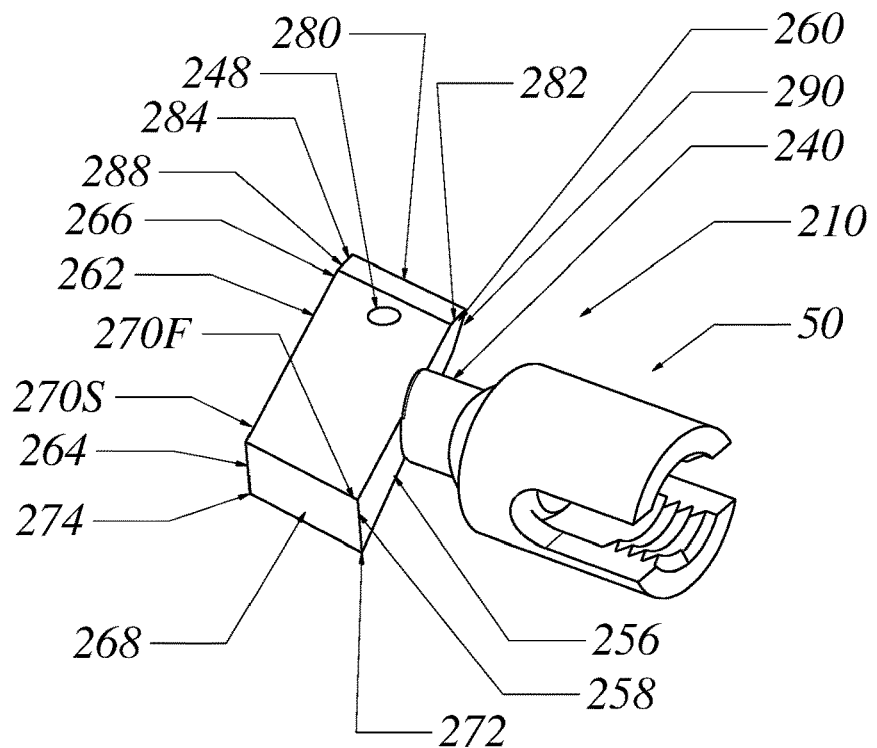
FIG. 14 is a perspective of a seventh preferred embodiment of the implant.
Figure 15:
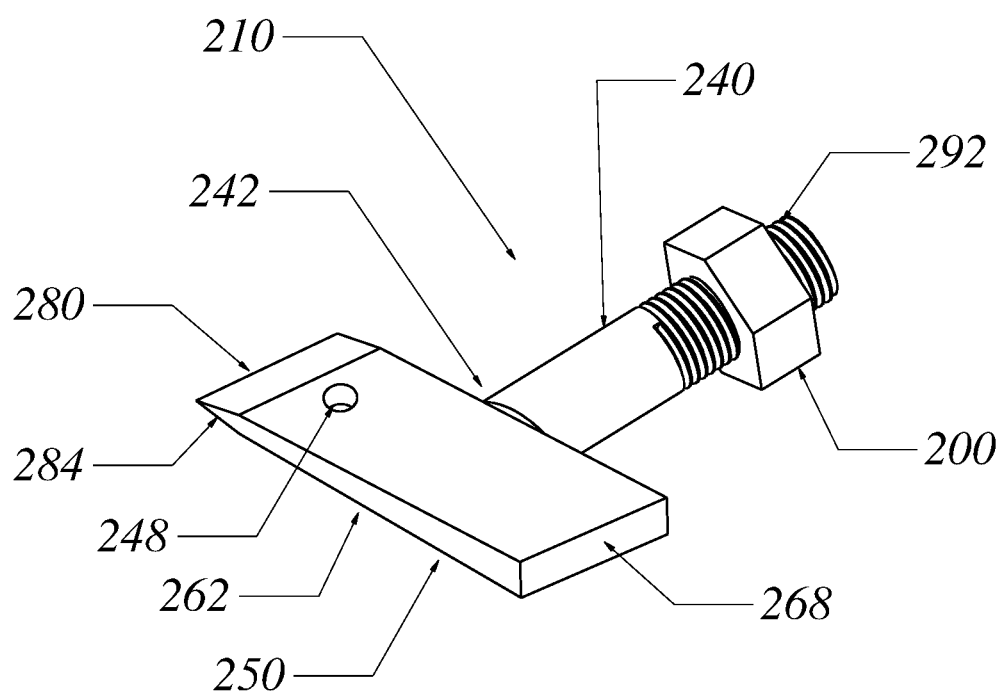
FIG. 15 is a perspective of an eighth preferred embodiment of the implant.

FIGS. 13-15 portray a seventh and eighth embodiments of the current invention. Implant (210) is adapted for interconnection with a device distinct from the implant (210). Examples of devices connectable to implant (210) include but are not limited to: rods, bars, cross-links, screws and locking nuts.

Implant (210) includes shaft (240) and surgical cutting wedge (250). In accordance with the present invention, cutting edge (280) of cutting wedge can cut in perpendicular, clockwise and counterclockwise directions relative shaft (240). By way of illustration, longitudinal motion of cutting edge (280) can penetrate and slice tissue(s) perpendicular to shaft (240) while rotation of shaft causes cutting edge (280) to cut tissue(s) in either a clockwise or counterclockwise directions. Select preferred embodiments of the current invention have a channel (248), positioned proximate to the cutting edge (280). Channel (248) extends through surgical cutting wedge (250). Among other things, channel (248) may allow passage of adhesives and bone growth substances through the shaft (240) and blade (250). Along with other openings of blade (250), channel (248) can increase the surface area to which bone may grow onto blade (250) which can increase stability of implant (210).

Shaft (240) has a first end (242) and a second end (244) opposite the first end (242). Select preferred embodiments of implant (210) can include a second end (286) of shaft (240) comprises a thread (292). Other preferred embodiments of implant (210) can include a polyaxial head (50) connected to second end (286) of shaft (240).

Surgical cutting wedge (250) is connected to the first end (242) of shaft (240). Within the ambit of the current invention, surgical cutting wedge (250) can be provided with first planar surface (252) and second planar surface (254). In select preferred embodiments, first side (256) of surgical cutting wedge (250) is connected with and perpendicular to the shaft (240). First side (256) of surgical wedge (250) has a first end (258) of greater height than an opposed second end (260) of first side (256). Second side (262) of surgical wedge (250) is parallel to the first side (256) and first end (264) of second side (262) is of greater height than opposed second end (266) of second side (262). Third side (268) of surgical cutting wedge (250) extends between the first and second planar surfaces (252, 254) and first and second sides (256, 262). In select preferred embodiments of implant (210), first and second planar surfaces (252, 254) can be parallelograms. Connection angles (270F, 270S) of first and second sides (256, 262) with opposed ends (272, 274) of the third side (268) can be identical.

Cutting edge (280) of surgical cutting wedge (250) can be opposed from and parallel to the third side (268) and connected to the first planar surface (252), the second planar surface (254) and the second ends (282, 284) of the first and second sides (256, 262). Slopes of first planar surface (252) and second planar surface (254) from the third side (268) to the cutting edge (280) can be utilized to establish one or more angles of surgical cutting wedge (250). Preferred embodiments of cutting edge (280) can include bevel (294).

Select preferred embodiments of cutting edge (280) have elevations of cutting edge (280) that are graduated from a greater height to a lesser height as the cutting edge (280) traverses from an outward margin (288) of the second end (284) of the second side (262) toward outward margin (290) of the second end (282) of the first side (256).

It is believed that surface treatments (276) of implant (210) improve resistance against pullout or back out of implant (220) when compared to currently available surgical screws.

Applicant has enabled, described and disclosed the invention as required by the Patent Cooperation Treaty and Title 35 of the United States Code.

What is claimed is:

1. An implant for bone adapted for interconnection with a device distinct from the implant; the implant comprising:
    a) a shaft comprising a first end and a second end opposite the first end; the shaft including a first longitudinal axis therein and extending away from the first end and the second end; and
    b) a surgical cutter comprising:
        i) a first segment extending away from the first longitudinal axis in a first direction and a second segment extending away from the first longitudinal axis in a second direction, wherein the first segment and the second segment include a second longitudinal axis;
        ii) a first surface and a second surface opposed from the first surface; the first and second surfaces separated by a thickness, wherein the first and second surfaces sandwich the thickness and the thickness is greater proximate the first longitudinal axis and lesser remote from the first longitudinal axis such that the first segment and the second segment comprise different slopes;
        iii) a first side connected, at an angle oblique to the first longitudinal axis, to a first end of the shaft;
        iv) a second side parallel to the first side for a length of the first segment;
        v) a third side extending between the first and second surfaces and first and second sides;
        vi) a fourth side extending between the first and second surfaces and the first and second sides, wherein the thickness is enclosed by the first and second surfaces and the first, second, third and fourth sides; and
        vii) at least one cutting edge incorporated onto the second side and the fourth side; the cutting edge connected to the first surface, the second surface, the second side and fourth side.

2. The implant of claim 1, wherein the cutting edge is adapted to cut in a forward, a clockwise or a counterclockwise direction.

3. The implant of claim 2, wherein the second segment of the surgical cutter comprises a bend.

4. The implant of claim 3, wherein the bend comprises a first curve away from the second longitudinal axis and a second curve toward the second longitudinal axis.

5. The implant of claim 4, wherein the second segment comprises a greater surface area than the first segment.

6. The implant of claim 3, wherein the cutting edge comprises a bevel.

7. The implant of claim 3 comprising a head connected to the second end of the shaft.

8. The implant of claim 7, wherein the head is a polyaxial head.

9. The implant of claim 3, wherein the second end of shaft comprises a thread.

10. The implant of claim 9 comprising surface treatments.

11. An implant for bone adapted for interconnection with a device distinct from the implant; the implant comprising:
    a) a shaft comprising a first end and a second end opposite the first end; the shaft including a first longitudinal axis; and
    b) a surgical cutter comprising:

i) a first surface and a second surface opposed from the first surface; the first surface and the second surface sandwiching a shared thickness; the shared thickness comprising a least one common bend;
ii) a first side connected, at an angle oblique to the first longitudinal axis, to a first end of the shaft;
iii) a second side parallel to the first side;
iv) a third side extending between the first and second sides;
v) a fourth side extending between the first and second sides; and
vi) at least one cutting edge incorporated onto the second side and the fourth side.

12. The implant of claim 11, wherein the cutting edge is adapted to cut in a forward, a clockwise or a counterclockwise direction.

13. The implant of claim 12; the thickness greater proximate the first longitudinal axis and lesser remote from the longitudinal axis, wherein a first segment of the surgical cutter is located on a first side of the first longitudinal axis and a second segment of the surgical cutter is located on a second side of the first longitudinal axis, thereby creating different slopes for the first and second segments.

14. The implant of claim 13, wherein the first segment and the second segment include a second longitudinal axis and the segment with a common bend comprising a greater surface area than the segment without the common bend.

15. The implant of claim 14, wherein the common bend comprises a first curve away from the second longitudinal axis and a second curve toward the second longitudinal axis.

16. The implant of claim 15, wherein the cutting edge comprises a bevel.

17. The implant of claim 16 comprising a head connected to the second end of the shaft.

18. The implant of claim 17, wherein the head is a polyaxial head.

19. The implant of claim 16, wherein the second end of shaft comprises a thread.

20. The implant of claim 16 comprising surface treatments.

21. An implant for bone adapted for interconnection with a device distinct from the implant; the implant comprising:
a) a surgical cutting wedge comprising:
i) a first planar surface and a second planar surface;
ii) an interconnected combination of a first side, a second side and a third side; the interconnected combination of the first, second and third sides extending between and connected to the first and second planar surfaces, wherein: the first side comprises a first end of greater height than an opposed second end of first side; and the second side comprises a first end of greater height than an opposed second end of the second side;
iii) a cutting edge connected to the first and second planar surfaces and the second ends of the first and second sides such that the cutting edge is adapted to cut in perpendicular, clockwise and counterclockwise directions relative to a shaft; and
iv) a channel, positioned proximate to the cutting edge, extending through the surgical cutting wedge; and
b) a first end of a shaft connected permanently to the first side of the surgical cutting wedge such that rotation of the shaft rotates the surgical cutting wedge.

22. The implant of claim 21 comprising a head connected to the second end of the shaft.

23. The implant of claim 22, wherein the head is a polyaxial head.

24. The implant of claim 21, wherein the second end of shaft comprises a thread.

* * * * *